US006666854B1

(12) United States Patent
Lange

(10) Patent No.: US 6,666,854 B1
(45) Date of Patent: Dec. 23, 2003

(54) ENDOSCOPIC SURGICAL INSTRUMENT

(75) Inventor: Grégoire Lange, Annecy (FR)

(73) Assignee: La Precision, Scionzier (FR)

( * ) Notice: Subject to any disclaimer, the term of this patent is extended or adjusted under 35 U.S.C. 154(b) by 73 days.

(21) Appl. No.: 10/009,606

(22) PCT Filed: Jun. 23, 2000

(86) PCT No.: PCT/FR00/01769

§ 371 (c)(1),
(2), (4) Date: Dec. 11, 2001

(87) PCT Pub. No.: WO01/00095

PCT Pub. Date: Jan. 4, 2001

(30) Foreign Application Priority Data

Jun. 25, 1999 (FR) .............................................. 99 08341

(51) Int. Cl.⁷ ................................................ A61B 17/00
(52) U.S. Cl. ............................ 606/1; 606/205; 606/208
(58) Field of Search ............................... 606/1, 51, 52, 606/205–211, 46, 174; 600/562, 564

(56) References Cited

U.S. PATENT DOCUMENTS

| | | | |
|---|---|---|---|
| 5,374,277 A | * 12/1994 | Hassler | ........................ 606/207 |
| 5,454,827 A | 10/1995 | Aust et al. | |
| 5,702,408 A | 12/1997 | Wales et al. | |
| 5,743,456 A | * 4/1998 | Jones et al. | ............... 227/176.1 |
| 5,827,323 A | 10/1998 | Klieman et al. | |

FOREIGN PATENT DOCUMENTS

| | | | |
|---|---|---|---|
| DE | 26 03 370 A1 | | 8/1977 |
| EP | 0 646 356 A2 | | 4/1995 |
| WO | PCT/US97/17328 | * | 4/1998 |
| WO | WO 98/14124 | | 4/1998 |

* cited by examiner

Primary Examiner—Michael Peffley
(74) Attorney, Agent, or Firm—Oliff & Berridge, PLC

(57) ABSTRACT

The present invention relates to an instrument for endoscopic surgical instrument. The invention is characterized by a single control element whose orientation enables the distal part of the instrument to be articulated at any angle, and whose rotation (about its own axis) enables the orientation of this distal part about its lengthwise axis to be controlled. The position of this single control element, in front of the handle, is ergonomic and reflects the simple rotation controls existing in the rigid, straight-line instruments available on the market and habitually used by surgeons. In general, the endoscopic surgical instrument comprises a gripping and control handle, an elongated tubular part, a ball joint, a terminal or distal part, and a tool carried by the end of distal part. In the handle is a controller, for controlling the tool attached to the end of the distal part, and an assembly for controlling the angle and/or orientation of the distal part, or at least of the attached tool, relative to the elongated tubular part, by joint. The assembly that controls the angle and orientation of distal part is located in the front part of handle, and this assembly, through manipulation of a single operating element, enables both the angle of distal part and the orientation of this part, or at least its terminal tool, to be controlled.

24 Claims, 8 Drawing Sheets

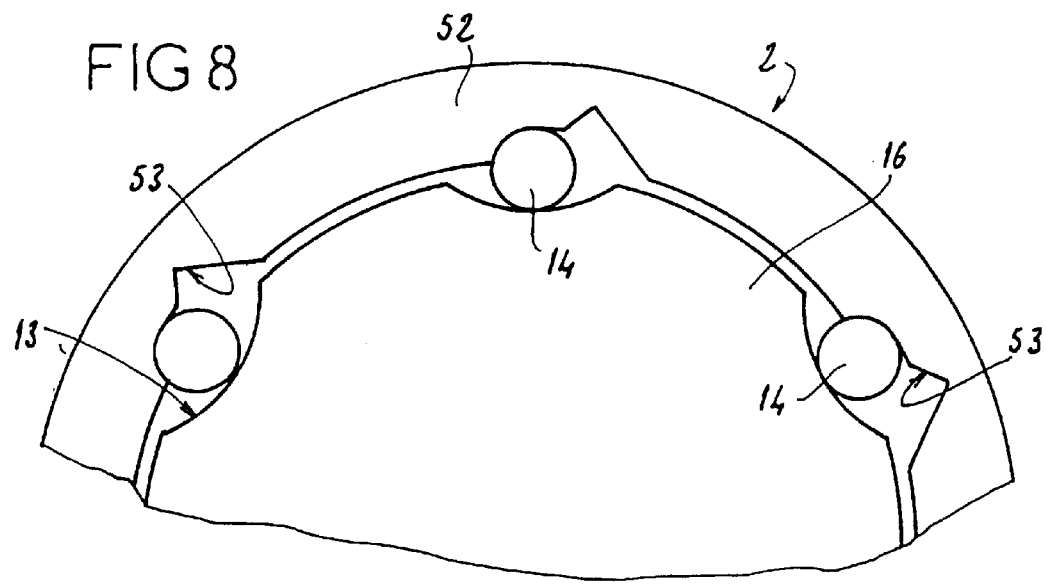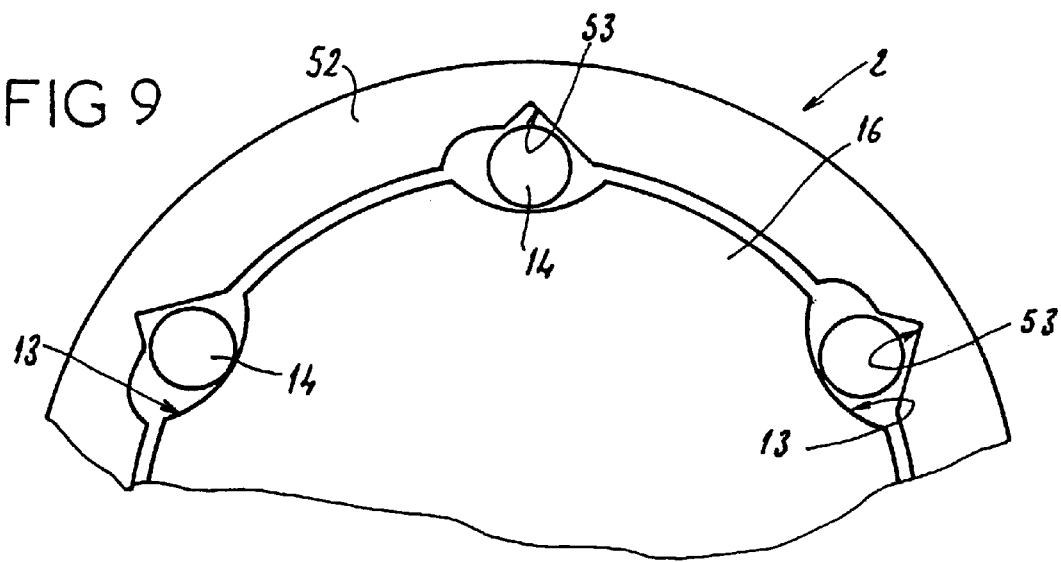

ENDOSCOPIC SURGICAL INSTRUMENT

BACKGROUND OF THE INVENTION

1. Field of Invention

The present invention relates to an instrument for endoscopic surgery with principal applications to laparoscopy (abdominal endoscopic surgery) and thoracoscopy (endoscopic surgery of the thorax).

2. Description of Related Art

This endoscopic surgical instrument belongs to the species of those having a handle extended by an elongated tubular part, itself connected by a multidirectional joint to a terminal or distal part able to carry a tool, control means being provided in the handle area to control the angle of the terminal part by means of a mechanical wire or cable transmission passing inside the tubular part, also traversed by a central tool control cable.

An endoscopic surgical instrument of this type is known from European Patent Application EP 0 646 356 A2. Because of its articulated distal end, such an instrument offers the surgeon access to a larger part of the surgical field, enabling him to choose the direction of approach and making the procedure more effective. This, the surgeon is freed of the constraints linked to endoscopic surgery, particularly passage through a fixed point (such as the point of entry into the abdomen).

However, the embodiment described and illustrated in the European patent application referred to above remains imperfect, and has in particular the following drawbacks:

In the embodiment subject of European Patent Application EP 0 646 356 A2, it is not possible to rotate the distal part of the instrument about its own lengthwise axis from the control element located on the handle. Moreover, this control element is located in the back part of the handle, which is a non-ergonomic position that could lead to inaccurate control.

When the above document is reduced to practice, at least in certain embodiments, the transmission wires have to be crossed, reversing the direction of movement of the distal end of the instrument relative to the control. Moreover, the crossing of the wires complicates their path and brings about friction. This crossing also reduces the free space available for controlling the tool on the instrument, for example the forceps opening and closure control.

Since the transmission wires of the instrument according to document EP 0 646 356 A2 are anchored to the ball joint of the distal part, the maximum authorized displacement remains relatively limited.

Moreover, in the instrument according to the aforesaid document, there is no provision for locking the orientation mechanism in any position that is to be temporarily maintained; thus, as soon as the control is released, the mechanism returns to the starting position (central position), urged by springs.

Finally, the instrument described in document EP 0 646 356 A2 is not impermeable, except for an O-ring located on the ball joint, and is difficult to clean.

SUMMARY OF THE INVENTION

The goal of the present invention is to eliminate all these drawbacks by providing an endoscopic surgical instrument that is improved both in its control, rendered particularly ergonomic, and in its utilization options, while ensuring impermeability.

For this purpose, the invention relates essentially to an endoscopic surgical instrument of the type referred to at the outset wherein:

the control means, located in the front part of the handle, comprise a spherical crown having a center and an axis, the crown being orientable in all directions inside a cone relative to its center and being rotatable about its axis, the spherical crown is linked at an angle to a part controlling wires or cables, the proximal ends of the transmission wires or cables being attached to said control part, means, are provided to transmit the rotation of the spherical crown about its axis to an internal element mounted to rotate about the axis of the elongated tubular part, rotation of this element being transmitted, through the aforesaid joint, to the terminal part in order to orient this terminal part around its own lengthwise axis, and means, are provided for non-permanent locking of the aforesaid joint at any angle.

Preferably, the spherical crown is connected to the internal element mounted to rotate about the axis of the elongated tubular part by means of a gimbal mechanism.

Thus, the invention provides an endoscopic surgical instrument, characterized mainly by a single control element whose orientation enables the distal part of the instrument to be articulated at any angle, and whose rotation (about its own axis) enables the orientation of this distal part about its lengthwise axis to be controlled. The position of this single control element, in front of the handle, is ergonomic and reflects the simple rotation controls existing in the rigid, straight-line instruments available on the market and habitually used by surgeons.

In one embodiment of the invention, the output element of the gimbal mechanism is coupled to the central tool-controlling cable by means of a gear train able to transmit the rotary movement from the outside of the elongated tubular part to the inside thereof, the gear train comprising a gear linked rotationally to the output element of the gimbal mechanism, another gear rotationally linked to a central rod linked to the tool-controlling cable, and intermediate pinions, engaging the aforesaid two gears.

According to another embodiment of the invention, the output element of the gimbal mechanism is coupled to the central tool-controlling cable by magnetic means, in particular permanent magnets, with interposition of a fixed nonmagnetic impermeable wall.

According to another embodiment of the invention, the output element of the gimbal mechanism is coupled directly to an internal rotating tubular element surrounding the tool-controlling cable and forming a rotating assembly with the latter.

According to a simple arrangement, the control spherical crown is itself the operating element activatable by the user.

However, in a preferred embodiment the spherical crown is surrounded concentrically with an external operating ring to which it is coupled angle- and rotation-wise by magnetic means, in particular permanent magnets, with interposition of a fixed nonmagnetic impermeable wall. This design of the control, with an external element manipulated by the surgeon, coupled to an internal control crown, provides a sealed design, as the magnetic coupling produced through the fixed impermeable wall allows identical positioning and movement of the spherical control crown and the operating ring without mechanical complications.

Since such an endoscopic surgical instrument is normally provided with a separate control to activate the tool carried by the instrument, particularly a control for opening and closing a forceps by a small-amplitude translational movement, additional sealing means are also provided in the form of flexible sleeves located in the proximal and distal parts. Since an internal sealing sleeve located at the distal part is subject to torsion when this distal part rotates about its lengthwise axis, this torsion has to be limited in order not to tear the sleeve. For this purpose, the instrument also advantageously has mechanical means for limiting the rotation of the distal part. In one particular embodiment, these means comprise a part mounted to rotate freely in the handle, said part being entrained rotationally by a first finger linked rotationally with the internal element receiving the rotational movement of the spherical crown, the aforesaid part itself having a second finger that abuts a fixed part. Such a mechanism allows rotation around slightly less than two complete turns.

According to another aspect of the invention, the multi-directional joint between the elongated tubular part and the terminal or distal part of this instrument comprises a free intermediate ball joint able to describe an orientation movement with respect to a female ball joint integral with the front end of the elongated tubular part and also with respect to another female ball joint integral with the back end of the terminal part of the instrument, all these ball joints being concentric, and the transmission wires or cables passing by the periphery of the intermediate ball joint, their front ends being connected to the terminal part of the instrument.

Thus, the instrument has a double intermediate ball joint, for example with a displacement of approximately ±30° for each of the two female ball joints relative to the intermediate ball joint so that the distal part can be oriented over approximately ±60° in all directions of space.

The intermediate ball joint preferably has a shaped diametral passage traversed by the central flexible tool-controlling cable carried by the instrument in order to guide this flexible cable which, itself, positions the intermediate ball joint at the ideal orientation corresponding to an angle equal to half the total angle between the elongated tubular part and the distal part. The appropriate guidance of the central flexible cable also ensures firm application of the two female ball joints against the intermediate ball joint, while avoiding a change in length of this cable during the angling to prevent any undesired opening or closure of the tool, particularly a forceps.

Advantageously, the back ends of the transmission wires or cables are anchored to an internal spherical control element whose diameter is greater than that of the intermediate ball joint, preferably a diameter equal to or double that of the intermediate ball joint; thus, the angular displacement of the control element is doubled at the distal part: a ±30° movement of the control element, compatible with the mechanical structure and with ergonomic requirements, allows the distal part to be oriented by ±60°.

According to another aspect of the invention, the instrument has means for locking the aforesaid joint, which is in particular a ball joint as defined above, hence means for immobilizing the terminal or distal part of the instrument at the angle given by the control means. Advantageously, the nonpermanent locking means of the joint between the elongated tubular part and the distal part of the instrument comprise elements that act by gripping the transmission wires or cables, these elements being located on said elongated tubular part, preferably at a relatively short distance from the joint, such as a ball joint, which increases its efficiency. Since the wires or cables must remain flexible to facilitate angling control, it is inappropriate to block these wires or cables near the control element, as lengthening of the wires or cables would impair the locking action.

According to one embodiment, the elements gripping the transmission wires or cables in order to lock the aforesaid joint comprise a ring with recesses mounted to rotate about the elongated tubular part and acting by simultaneously jamming all the wires or cables, themselves positioned in lengthwise recesses in the main body of the elongated tubular part. Limited rotation of the ring in a chosen direction locks the transmission wires or releases them.

According to another embodiment, the means gripping the transmission wires or cables in order to lock the aforesaid joint comprise a jamming ring or sleeve mounted to slide in the axial direction of the elongated tubular part and having a frustroconical part acting on the wires or cables. This variant permits "automatic" locking and unlocking control; in particular, unlocking occurs as soon as the control element is activated.

In one particular embodiment, the assembly controlling the angle and rotation of the distal part is translationally movable along the axis of the elongated tubular part and, by means of a cam, controls the jamming and release of the transmission wires or cables, in the case of a rotary jamming ring as described above.

The instrument that is the subject of the invention may also include buttress type locking means located on the handle that act on the axially movable central rod that is connected to the tool control cable in order to maintain the position of this tool, particularly the closure of a forceps.

BRIEF DESCRIPTION OF THE DRAWINGS

The invention will be better understood with the aid of the description that follows, with reference to the attached schematic drawing showing several embodiments of this endoscopic surgical instrument as examples:

FIGS. 8 and 9 are views illustrating the joint locking means in two positions.

DETAILED DESCRIPTION OF THE PREFERRED EMBODIMENTS

Figure 1:
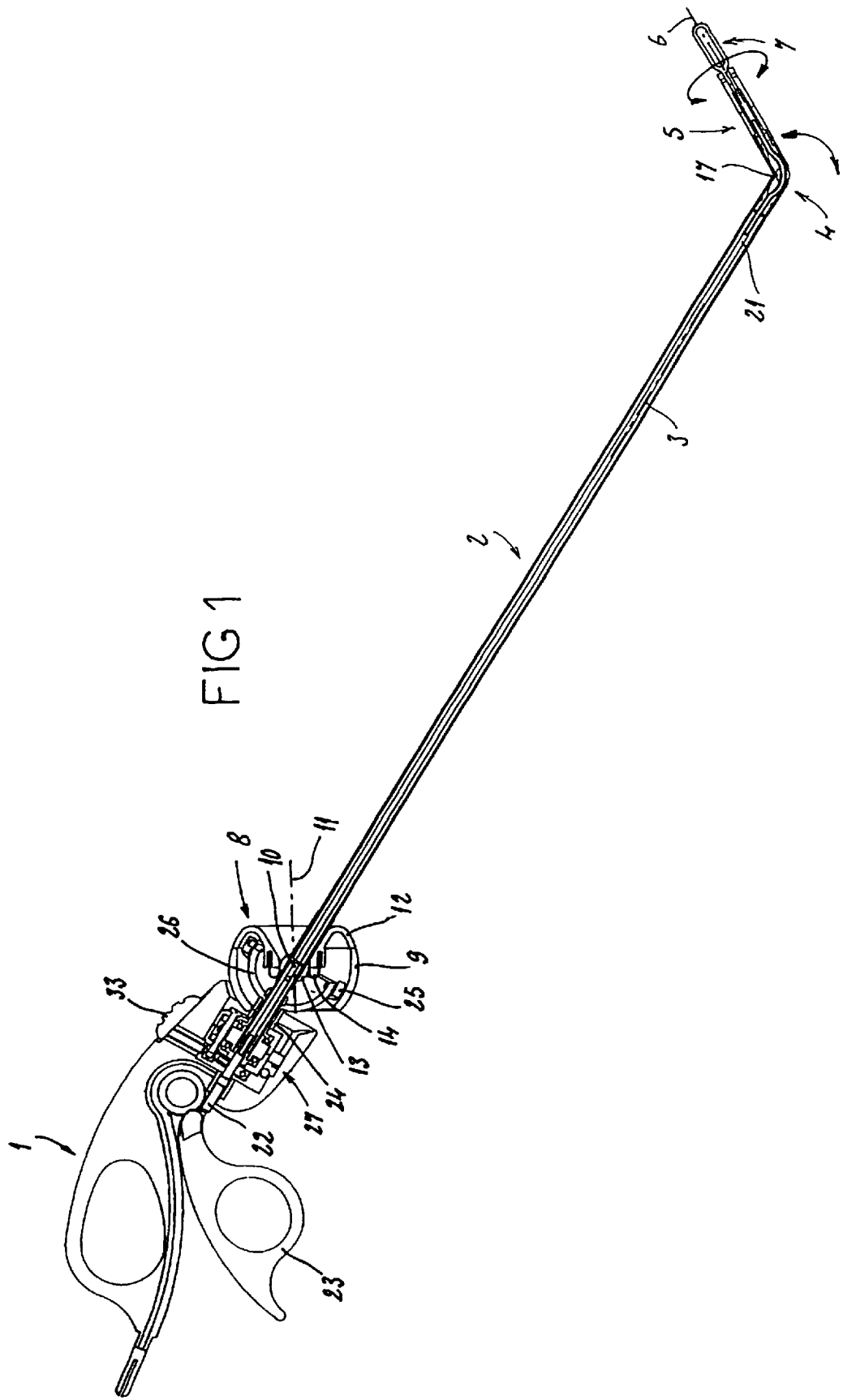
FIG. 1 is a general view in lengthwise section of an endoscopic surgical instrument according to the present invention in a first embodiment.

The endoscopic surgical instrument shown in the drawing has in general, from back to front: a gripping and control handle 1, an elongated tubular part 2 with a lengthwise axis 3, a ball joint 4, a terminal or distal part 5 with a lengthwise axis 6, and a tool 7 carried by the end of distal part 5. Handle 1 has a part controlling tool 7, in particular for controlling the opening/closing of this forceps-shaped tool 7, and an assembly 8 for controlling the angle of the distal part 5 relative to the elongated tubular part 2, by joint 4. Assembly 8 also controls the orientation of the distal part 5, or at least of its terminal tool 7, around its own lengthwise axis 6. According to essential features of the invention, assembly 8 that controls the angle and orientation of distal part 5 is located in the front part of handle 1, and this assembly 8, through manipulation of a single operating element, enables both the angle of distal part 5 and the orientation of this part, or at least its terminal tool 7, to be controlled.

This control gives rise to various embodiments depending on the degree of impermeability desired and the associated functions performed, such as locking distal part 5 at the given angle.

Figure 2:
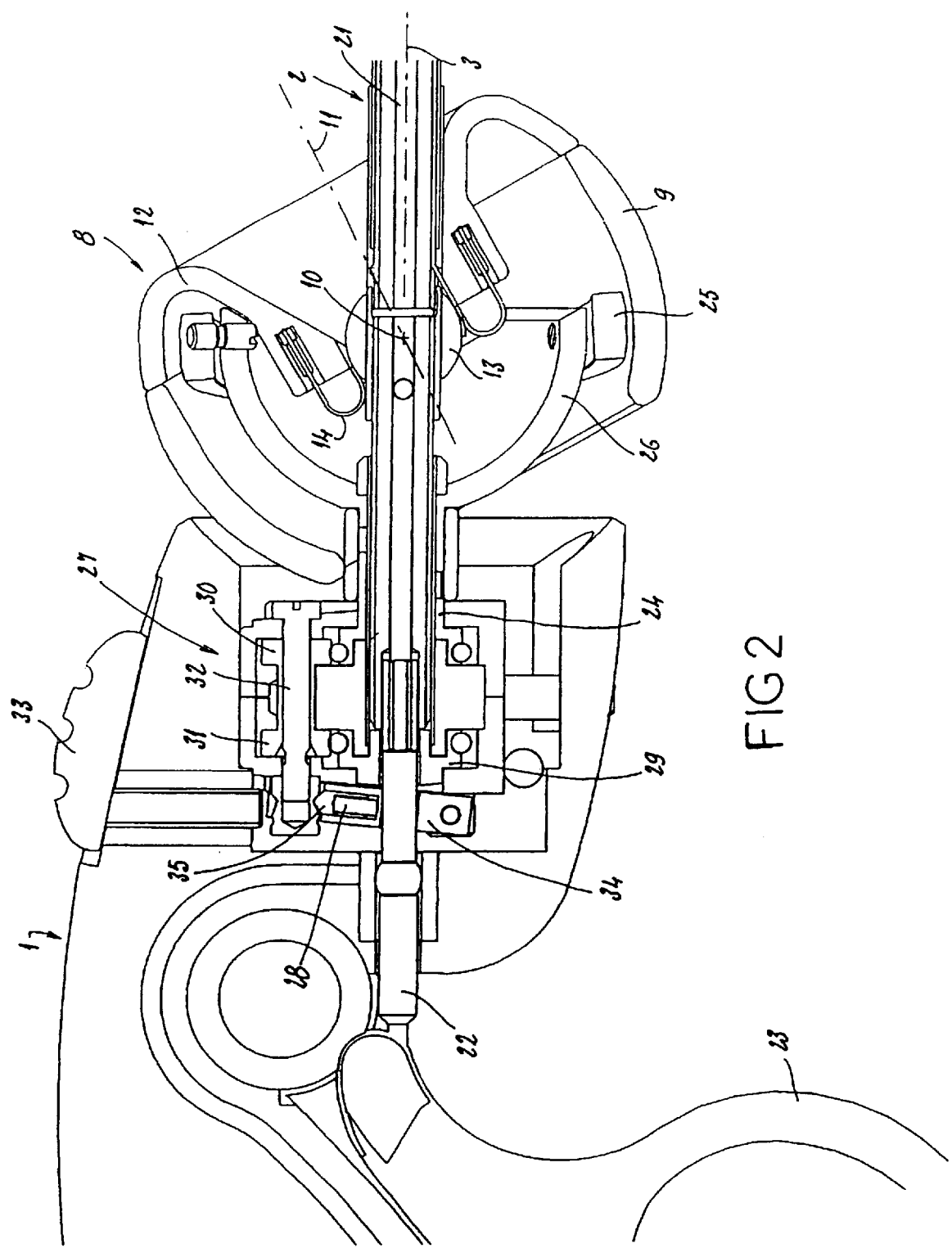
FIG. 2 is a view in lengthwise section on a larger scale of the handle area of this instrument.
Figure 3:
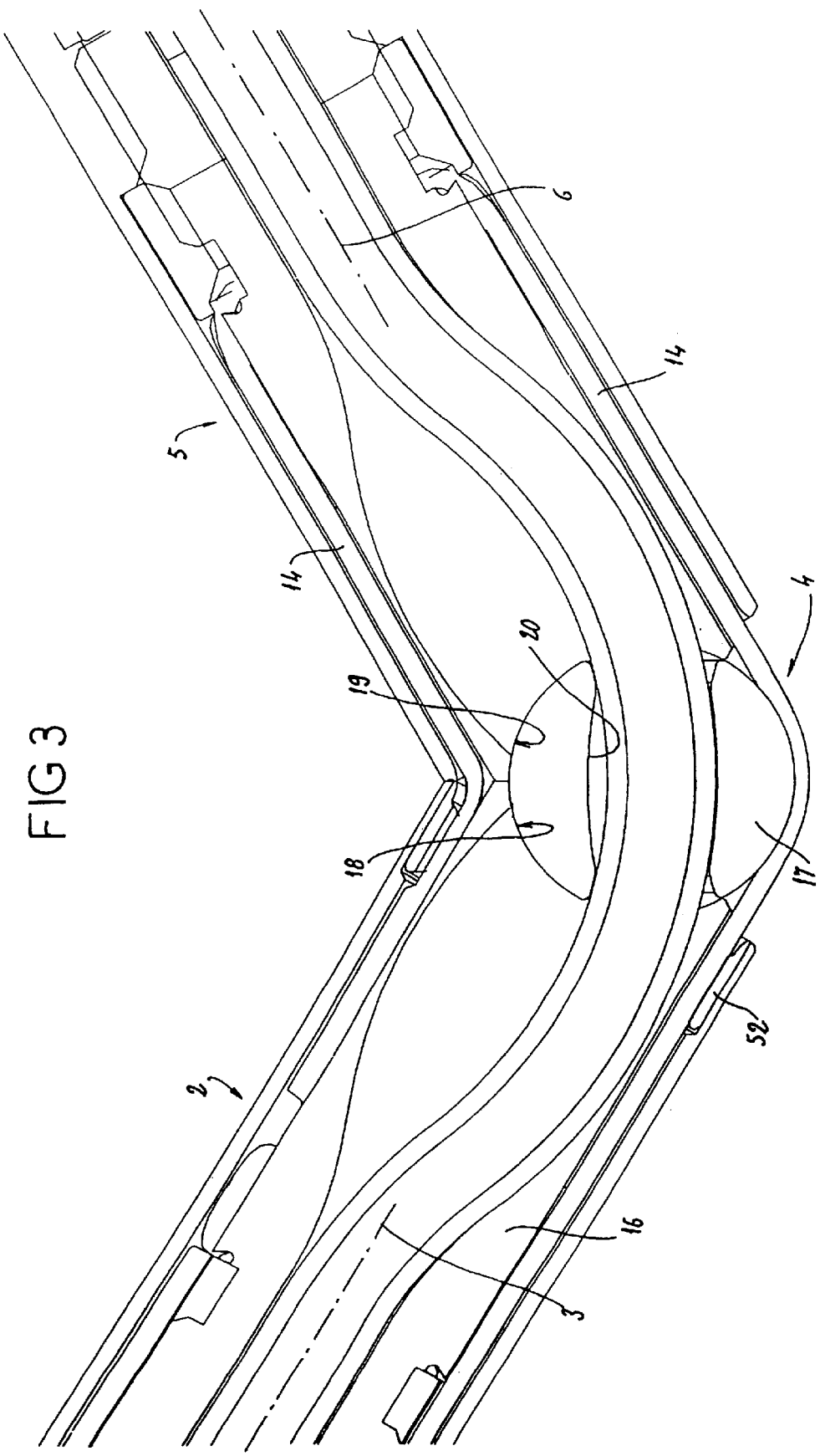
FIG. 3 is a detailed view of the joint region of this instrument.

In the embodiment in FIGS. 1 to 3, control assembly 8 has a spherical crown 9 of which the center is indicated at 10 and the axis of revolution at 11. Spherical crown 9 is completed in the frontal and inward direction by a part 12 with conical clearance, amounted around a central spherical part 13, traversed by the elongated tubular part 2.

On part 12, orientable in all directions (inside a cone) around center 10, there are anchored the back ends of transmission cables 14, six in number. Transmission cables 14 extend longitudinally inside the elongated tubular part 2 in recesses 15 provided at regular angular intervals in the main body 16 of this part—see FIGS. 8 and 9.

Joint 4 between the elongated tubular part 2 and distal part 6, has a free intermediate ball joint 17 which cooperates with two opposite female ball joints 18 and 19. The first female ball joint 18 is integral with the front end of the elongated tubular part 2. The second female ball joint 19 is integral with the back end of distal part 5.

The six transmission cables 14 pass by the periphery of intermediate ball joint 17 and their front ends are connected to distal part 5. In fact, for manufacturing reasons, the six cables 14 are advantageously only three cables, each of which is bent back forward. The simultaneous movement of these cables 14 is controlled by part 12 and the cables thus displaced slide on the central spherical part 13 before engaging the aforementioned recesses 15. The diameter of spherical part 13 is double the diameter of intermediate ball joint 17; thus, the angular displacement of part 12 is doubled on the articulated distal part 5. For example, at a maximum displacement angle of 60° at the control assembly 8, there is a maximum angular displacement of 60° of the distal part 5 relative to axis 3 of the elongated tubular part 2.

Intermediate ball joint 17 has a shaped diametral passage 20 traversed by a flexible cable 21 connecting the proximal area of the instrument to distal part 5, and which is used to control the opening/closing of tool 7. Flexible cable 21 is guided, at joint 4, by passage 20 of the intermediate ball joint, and this flexible cable 21 itself positions intermediate ball joint 17 at an angle half-way between the angles of the two female ball joints 18 and 19.

The back end of flexible cable 21 is integral with a rod 22 mounted to move axially in handle 1 and activatable by a trigger 23 belonging to this handle 1.

Spherical crown 9 of control assembly 8 is coupled to a tubular internal element 24 mounted to rotate about axis 3 by means of a gimbal mechanism comprising an intermediate ring 25 articulated to crown 9, and a hemispherical output element 26 articulated to intermediate ring 25 and integral with the aforesaid internal element 24.

A gear or friction gear train designated overall by 27 couples element 24 rotationally with rod 22 in order to transmit the movement from the outside of elongated tubular part 2 to the inside thereof. This gear train 27, which forms a housing located in handle 1 to the rear of control assembly 8, has a first wheel attached to element 24, a second wheel attached to a rotating element 29 in sliding linkage with rod 22, and intermediate pinions 30, 31 mounted in a peripheral position on shafts 32 parallel to central axis 3 in the manner of fixed planetary pinions (three pairs of pinions 30, 31 being provided for example).

Handle 1 also has a manual control 33 for locking/unlocking rod 22, and hence the cable 21 controlling tool 7, with a buttressing device. This device is comprised of a pivoting part 34 that can press against rod 22, provided with a pin 35 which is urged by a spring 28, which keeps it pressed against a cam 36 with a specific profile, in this case provided in the extension of one of the shafts 32 bearing pinions 30, 31. Cam 36 has a conical part which corresponds to the buttressing and hence the locking, and a straight part that allows this device to be decoupled.

Rotation of spherical crown 9 about its axis 11 causes, through the intermediary of gimbal mechanism 25, 26 and gear train 27 described above, a corresponding rotation of rod 22 about axis 3, which rotation is transmitted by flexible cable 21 to the distal part 5 in order to orient tool 7 around the lengthwise axis 6 of this distal part 5.

Here, the control assembly 8 is displaceable translationally over a short path in the direction of axis 3 of elongated tubular part 2. The user pulls this assembly 8 rearward to release transmission cables 14 and enable them to be angled, via a cam which converts the translational movement into rotation.

Finally, it should be noted that, in control assembly 8, spherical crown 9 and part 12 completing this crown have a common ball joint movement around center 10, but only crown 9 is driven rotationally about axis 11.

Figure 4:
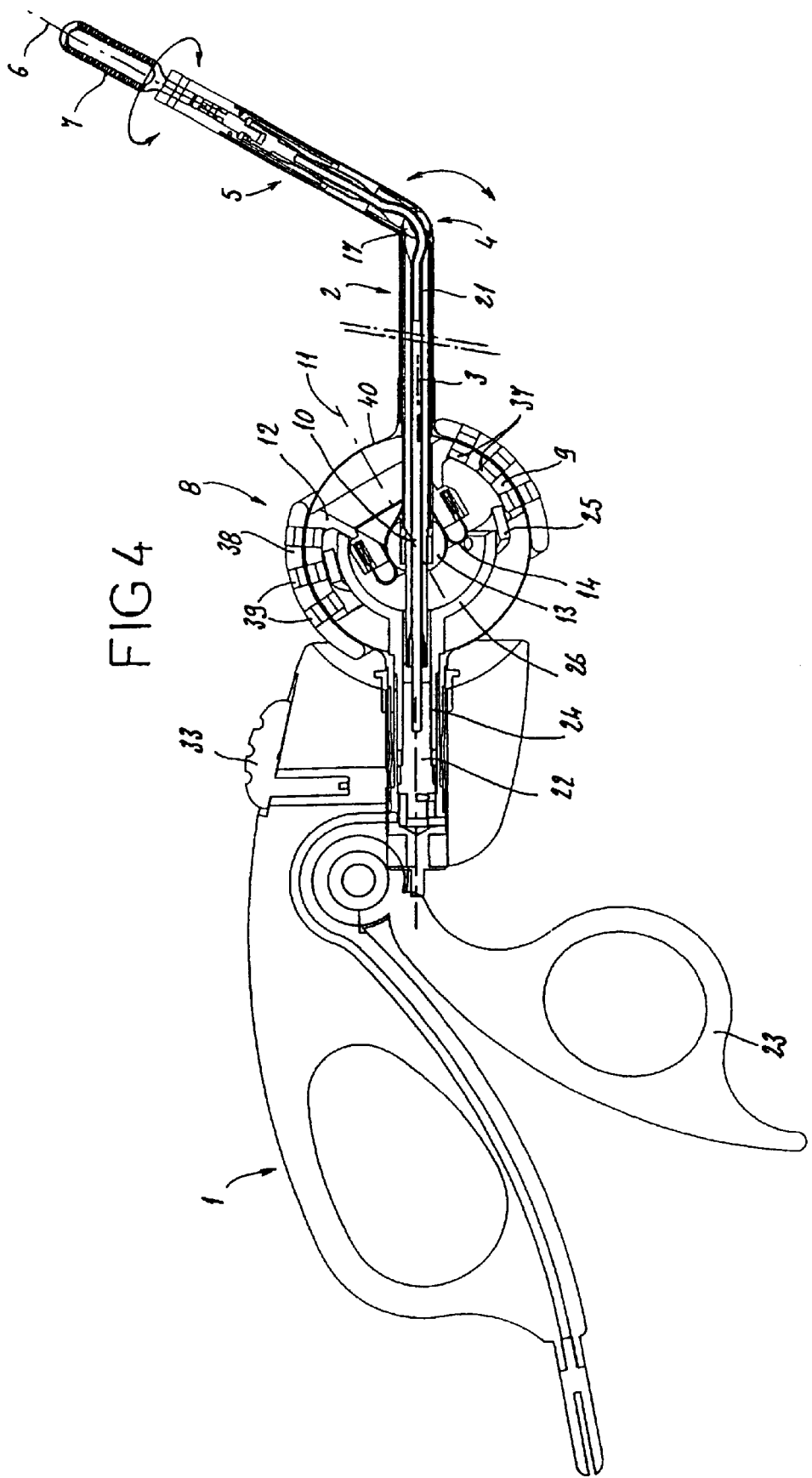
FIG. 4 is a general view in lengthwise section of a second embodiment of the instrument according to the invention.
Figure 5:
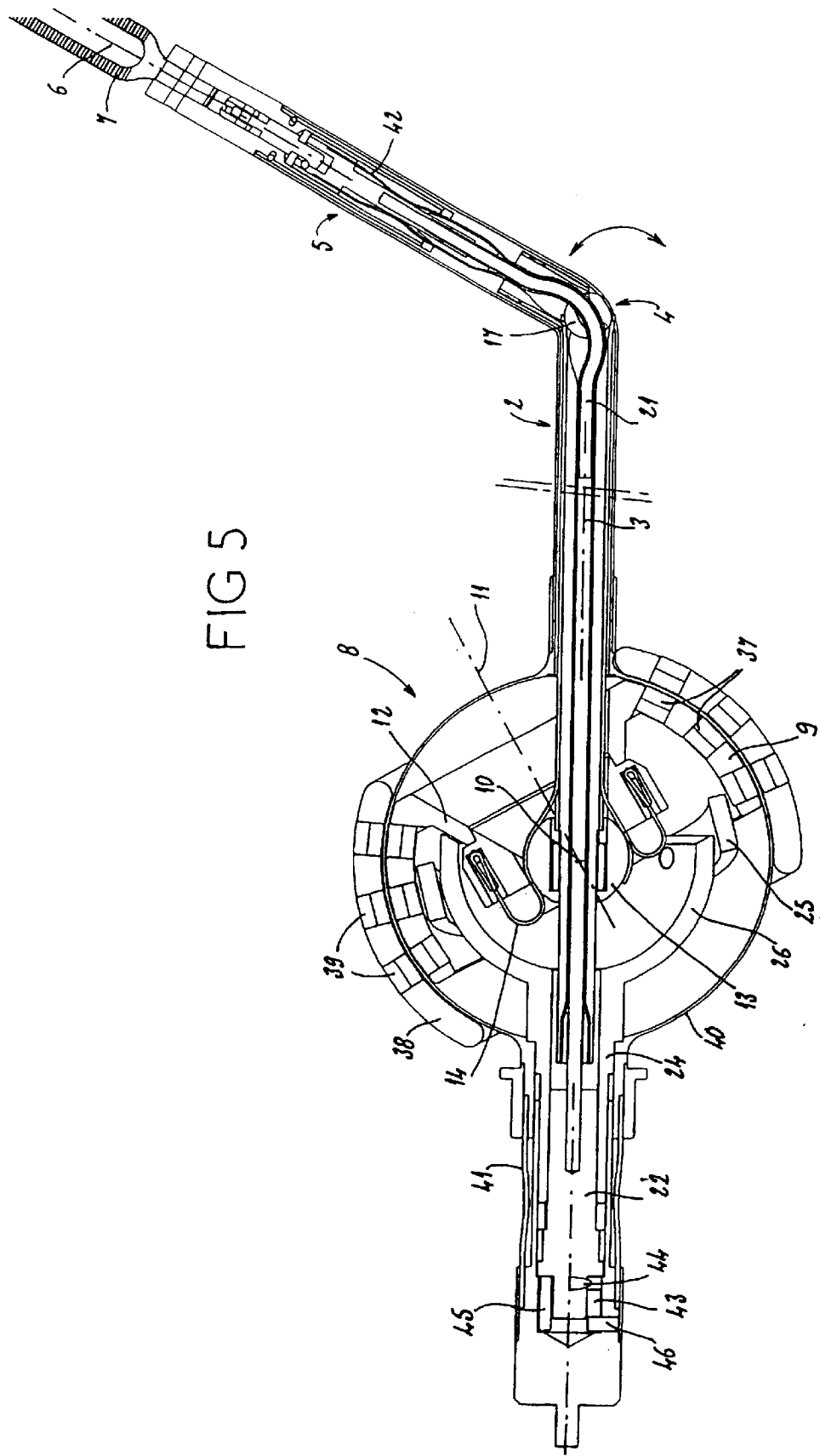
FIG. 5 is a lengthwise sectional view on a larger scale of the mechanism of the instrument in FIG. 4.

FIGS. 4 and 5 represent a second embodiment of the instrument. The elements in common with those in the preceding embodiment, or corresponding to them, are designated by the same numerals.

In particular, this embodiment also has a control assembly 8 with a spherical crown 9 orientable around its center 10 and rotating about its axis 11, enabling distal part 5 to be oriented and causing rotation of this distal part 5, or at least of terminal tool 7, about axis 6. Spherical crown 9 here is integral with part 12 with a conical clearance mounted around central spherical part 13.

Permanent magnets 37 are inserted into spherical crown 9. Spherical crown 9 is surrounded concentrically by an external operating ring 38, which is also shaped like a spherical crown. Other permanent magnets 39 are inserted into operating ring 38, and the number and arrangement of these correspond to magnets 37 of spherical crown 9. A fixed impermeable wall 40, spherically shaped and made of nonmagnetic material, extends between spherical crown 9 and operating ring 38. Thus, magnets 37 and 39 ensure magnetic coupling between operating ring 38 and spherical crown 9 through impermeable wall 40 so that the two parts supporting the magnets come into position and are moved identically on either side of impermeable wall 40.

Spherical crown 9, in this case activated by operating ring 38, once again controls the angle of distal part 5 through cables 14, and the orientation of this distal part 5 or tool 7 through a gimbal mechanism 25, 26, as described above. Output element 26 of the gimbal mechanism however drives rod 22 rotationally (i.e. without passing through a gear), said rod being integral with the back end of cable 21 that controls tool 7.

Since in this case the opening/closing control of tool 7 requires a small translation, it is necessary also to provide a seal on the proximal and distal parts, by flexible sleeves, 41 and 42 respectively. Sleeve 41 located in the proximal part accepts a small amount of translation due to the opening/closing control of tool 7. On the other hand, it is necessary to limit the rotation of the distal part 5 along axis 6 in order not to tear flexible sleeve 42 located in the distal area. For this purpose, at handle 1, an annular part 43 is provided, mounted freely rotationally around axis 3 and driven rotationally by a finger 44 integral with rod 22. Part 43 has another finger 45 which abuts a fixed stop 46. Rotation of rod 2, and hence of flexible cable 21, is thus limited to slightly less than two rotations.

Figure 6:
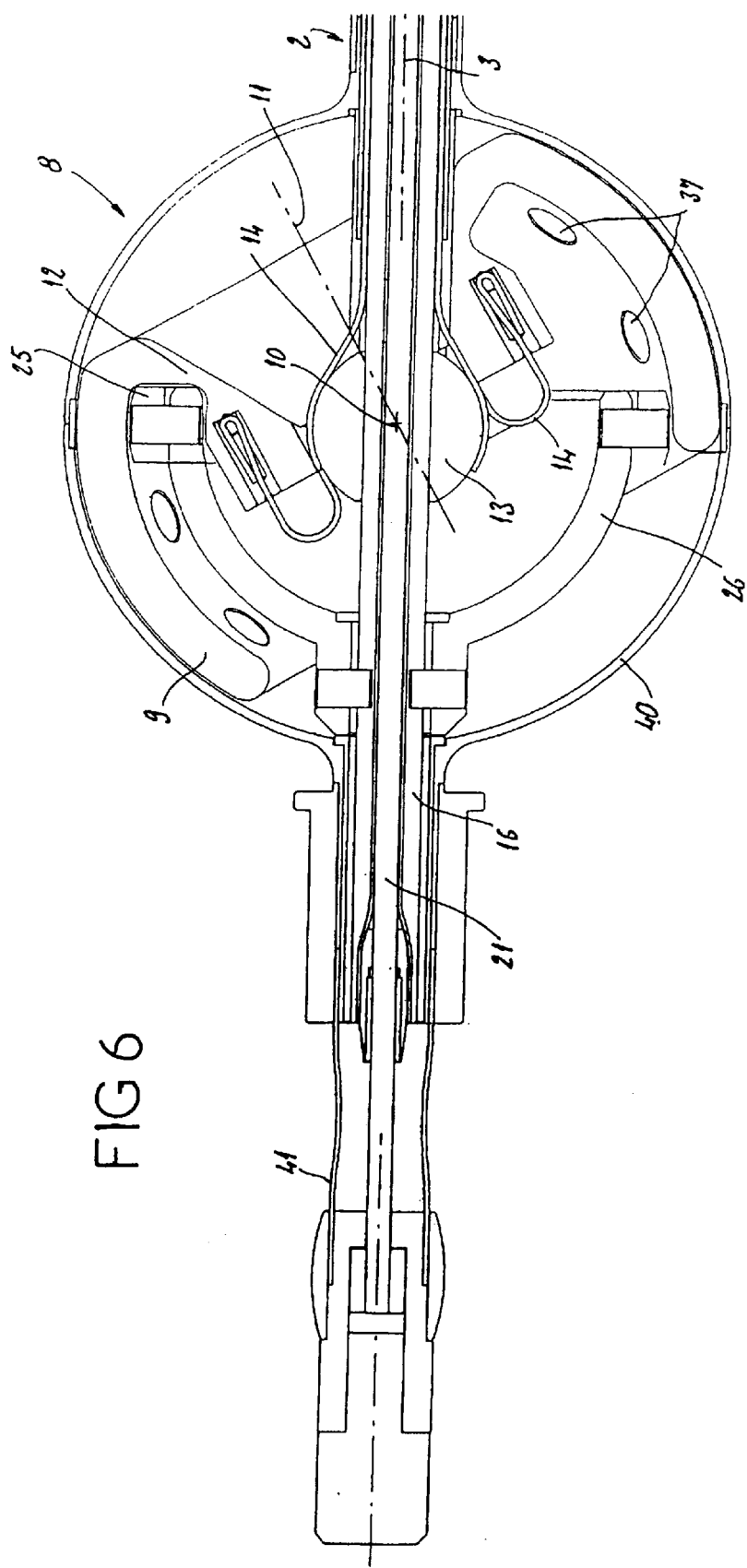
FIG. 6 is a partial view, in cross section, of one variant of the instrument in FIGS. 4 and 5.

FIG. 6 shows a variant of the previous embodiment in which the output element 26 of the gimbal mechanism is rendered directly integral with an internal tubular element 16 rotating inside the elongated tubular part 2 at the same time as flexible cable 21 that controls tool 7. This embodiment is impermeable, like the previous embodiment, and particularly simple.

Figure 7:
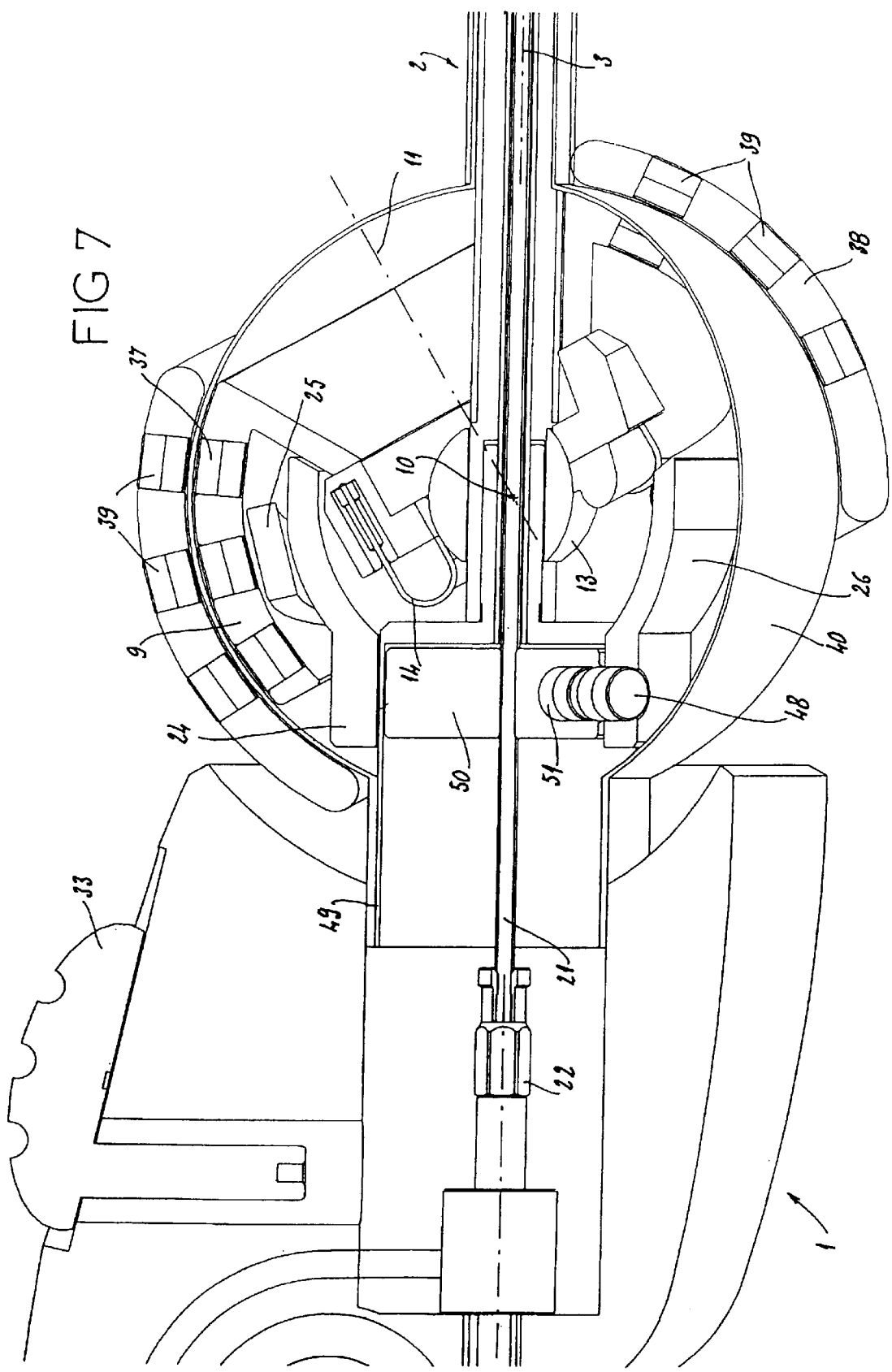
FIG. 7 is a partial view, in cross section, of another variant of this instrument.

Finally, FIG. 7 shows another variant in which output element 26 of the gimbal mechanism is coupled to flexible cable 21 (or to its terminal rod 22) by magnetic means. The output element 26 has a tubular extension into which permanent magnets 48 are inserted. A fixed impermeable wall 49 made of nonmagnetic material is surrounded by said tubular extension with magnets 48. Inside impermeable wall 49 a cylindrical part 50 is mounted, linked rotationally to flexible cable 21, other permanent magnets 51 being inserted into cylindrical part 50, with their number and arrangement corresponding to magnets 48 in output element 26. Thus, magnets 48 and 51 ensure magnetic coupling between output element 26 and part 50 so that the two parts occupy corresponding angular positions at all times. The latter embodiment is also impermeable, and even doubly impermeable (impermeable walls 40 and 49). Moreover, unlimited rotation of flexible cable 21 and hence of tool 7 is possible here.

FIGS. 8 and 9 illustrate an embodiment of the means which, by gripping transmission cables 14, temporarily lock the distal part 5 in any given orientation conferred on this distal part 5 by control assembly 8. As already mentioned above, cables 14 pass into lengthwise recesses 15 of main body 16 of the elongated tubular part 2. Around this main body 16, toward the end of tubular part 2 next to joint 4, is a rotating locking ring 52 (see also FIG. 3), this ring also being provided with V-shaped recesses 53 corresponding to cables 14. Depending on its angular position, ring 52 locks cables 14 by gripping (FIG. 8) or releases these cables 14 (FIG. 9). Gripping of the cables ensures locking of joint 4, and hence the angle of distal part 5. On the other hand, the release of cables 14 allows them to transmit the movement imparted by control assembly 8 to modify the angle of distal part 5.

While the invention has been described in conjunction with the exemplary embodiments outlined above, it is evident that many alternatives, modifications and variations will be apparent to those skilled in the art. Appropriate modifications may be made to the invention as needed depending on the type of tool used or the surgical procedure in which the instrument is used. Such modifications may include, for example, modifying the details of the various mechanical or magnetic devices of the instrument, replacing the rotating cable locking ring by a sliding locking sleeve, acting on the cables by a frustroconical part, replacing the terminal forceps by any other appropriate tool, or providing robotic or electronic, rather than manual, control without altering the overall control design, particularly in an impermeable embodiment. Accordingly, the exemplary embodiments of the invention as set forth above are intended to be illustrative, not limiting. Various changes may be made without departing from the spirit and scope of the invention as defined in the following claims.

What is claimed is:

1. An endoscopic surgical instrument, comprising:
    a handle extended by an elongated tubular part, itself connected by a multidirectional joint to a terminal or distal part that carries a tool,
    a control means being provided in the area of said handle to control articulation of the terminal part through a mechanical wire or cable transmission, having a front end and a back end, passing inside the tubular part, also traversed by a central cable controlling tool, wherein the control means, located in the front part of the handle, comprises a spherical crown having a center and an axis, the spherical crown being orientable in all directions inside a cone relative to its center and being rotatable about its axis and is linked at an angle to a control part controlling the wire or cable transmission, and the proximal ends of the wire or cable transmission are attached to said control part,
    a transmission means to transmit the rotation of the spherical crown about its axis to an internal element rotatably mounted about the axis of the elongated tubular part, and rotation of this element is transmitted through said joint to the terminal part in order to orient the terminal part around its own lengthwise axis, and
    a locking means for non-permanent locking said joint at any angle.

2. The endoscopic surgical instrument according to claim 1, wherein the spherical crown is connected to the internal element rotatably mounted about the axis of the elongated tubular part by a gimbal mechanism.

3. The endoscopic surgical instrument according to claim 2, wherein:
    the output element of the gimbal mechanism is coupled to the central cable controlling tool by means of a gear train able to transmit the movement from the outside of the elongated tubular part to the inside thereof, and
    the gear train comprises a first gear rotatably linked to the output element of the gimbal mechanism, a second gear is rotatably linked to a central rod linked to the cable controlling tool, and intermediate pinions engage the two gears.

4. The endoscopic surgical instrument according to claim 2, wherein the output element of the gimbal mechanism is magnetically coupled to the central cable controlling tool and a fixed nonmagnetic impermeable wall is interposed between the output element and the central cable controlling tool.

5. The endoscopic surgical instrument according to claim 2, wherein the output element of the gimbal mechanism is coupled directly to an internal rotating tubular element surrounding the cable controlling tool and forming a rotatable assembly with the cable controlling tool.

6. The endoscopic surgical instrument according to claim 1, wherein the spherical crown is itself the operating element activatable by the user.

7. The endoscopic surgical instrument according to claim 1, wherein the spherical crown is surrounded concentrically with an external operating ring to which it is magnetically coupled, and a fixed nonmagnetic impermeable wall is interposed between the spherical crown and the external operating ring.

8. The endoscopic surgical instrument according to claim 1, wherein the sealing means are flexible sleeves located in the proximal and distal parts of the instrument, and means for limiting the rotation of the distal part about its lengthwise axis are provided.

9. The endoscopic surgical instrument according to claim 8, wherein the means for limiting the rotation of the terminal or distal part about its axis comprises a part mounted to rotate freely in the handle, said part being entrained rotationally by a first finger linked rotationally with the internal element receiving the rotational movement of the spherical crown, said part itself having a second finger that abuts a fixed part.

10. The endoscopic surgical instrument according to claim 1, wherein the joint between the elongated tubular part and the terminal or distal part of the instrument comprises a free intermediate ball joint able to describe an orientation movement with respect to a first female ball joint integral with the front end of the elongated tubular part and also with respect to a second female ball joint integral with the back end of the terminal part of the instrument, both the first and second female ball joints are concentric, and the transmission wires or cables pass by the periphery of the intermediate ball joint and are connected by their front ends to the terminal part of the instrument.

11. The endoscopic surgical instrument according to claim 10, wherein both the first and second female ball joints each have a displacement of approximately ±30° with respect to the intermediate ball joint such that the distal part can be oriented over approximately ±60° in all directions of space.

12. The endoscopic surgical instrument according to claim 10, wherein the intermediate ball joint has a shaped diametral passage traversed by the central flexible cable controlling tool carried by the instrument in order to guide the flexible cable, which positions the intermediate ball joint.

13. The endoscopic surgical instrument according to claim 10, wherein the transmission wires or cables have their back ends anchored on an internal spherical control element, which has a larger diameter than that of the intermediate ball joint.

14. The endoscopic surgical instrument according to claim 1, wherein the nonpermanent locking means of joint between the elongated tubular part and the distal part of the instrument comprise gripping elements that grip the transmission wires or cables, the elements are located on said elongated tubular part.

15. The endoscopic surgical instrument according to claim 14, wherein the gripping elements that lock said joint comprise a ring with recesses mounted to rotate about the elongated tubular part and simultaneously jams all the wires or cables, themselves positioned in lengthwise recesses of the main body of elongated tubular part.

16. The endoscopic surgical instrument according to claim 14, wherein the gripping elements that lock said joint comprise a jamming ring or sleeve slidably mounted in the axial direction of the elongated tubular part and have a frustroconical part acting on the wires or cables.

17. The endoscopic surgical instrument according to claim 15, wherein the assembly controlling the orientation of the distal part is translationally movable along the axis of the elongated tubular part and controls the jamming and releasing of the transmission wires or cables by means of a cam.

18. The endoscopic surgical instrument according to claim 1, wherein a buttress type locking means located on the handle is provided that acts on an axially movable central rod connected to the control cable of the tool in order to maintain the position of the tool.

19. The endoscopic surgical instrument according to claim 1, characterized in that it has a robot control.

20. The endoscopic surgical instrument according to claim 4, wherein the output element of the gimbal mechanism is magnetically coupled to the central cable controlling tool by permanent magnets.

21. The endoscopic surgical instrument according to claim 7, wherein the spherical crown is surrounded concentrically with an external operating ring to which it is magnetically coupled by permanent magnets.

22. The endoscopic surgical instrument according to claim 13, wherein the diameter of the internal spherical control element is twice that of intermediate ball joint.

23. The endoscopic surgical instrument according to claim 14, wherein the gripping elements are located a short distance from the joint.

24. The endoscopic surgical instrument according to claim 18, wherein the buttress type locking means closes forceps.

* * * * *